US009535001B2

(12) United States Patent
Kuninori et al.

(10) Patent No.: US 9,535,001 B2
(45) Date of Patent: Jan. 3, 2017

(54) CELL COUNTING METHOD, CELL COUNTING DEVICE, AND COMPUTER-READABLE MEDIUM STORING CELL COUNTING PROGRAM

(71) Applicant: Toyo Seikan Group Holdings, Ltd., Tokyo (JP)

(72) Inventors: Masahiro Kuninori, Yokohama (JP); Ryo Suenaga, Yokohama (JP); Kyohei Ota, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 14/340,125

(22) Filed: Jul. 24, 2014

(65) Prior Publication Data
US 2016/0025612 A1    Jan. 28, 2016

Related U.S. Application Data

(63) Continuation of application No. PCT/JP2013/000290, filed on Jan. 22, 2013.

(30) Foreign Application Priority Data

Jan. 31, 2012  (JP) .................................. 2012-018403

(51) Int. Cl.
*G06K 9/00*     (2006.01)
*G01N 15/14*    (2006.01)
(Continued)

(52) U.S. Cl.
CPC ....... *G01N 15/1463* (2013.01); *G06K 9/00127* (2013.01); *G06K 9/6218* (2013.01);
(Continued)

(58) Field of Classification Search
None
See application file for complete search history.

(56) References Cited

U.S. PATENT DOCUMENTS

| 7,056,746 B2* | 6/2006 | Seul .................... B01J 19/0046 422/503 |
| 2004/0002131 A1* | 1/2004 | Kim ..................... B01L 3/5025 435/33 |

(Continued)

FOREIGN PATENT DOCUMENTS

| CN | 1837819 A | 9/2006 |
| CN | 102184420 A | 9/2011 |

(Continued)

OTHER PUBLICATIONS

M. Beals et al. "Cell Aggregation and Sphere Packing", Jan. 2010, pp. 1-5, <http://www.tiem.utk.edu/~gross/bioed/webmodules/spherepacking.htm>.*

(Continued)

*Primary Examiner* — Vu Le
*Assistant Examiner* — Samah Beg
(74) *Attorney, Agent, or Firm* — Osha Liang LLP

(57) ABSTRACT

To enable accurate counting the number of cultured cells without pulling apart cell clusters even if cells are aggregated densely to form three-dimensional cell clusters. An image of cultured cells is acquired, and from this image, an image of cell clusters and an image of individual cells are separated. Based on each of the image of cell clusters and the image of individual cells, the number of cells in the cell cluster and the number of individual cells are calculated.

10 Claims, 6 Drawing Sheets

(51) Int. Cl.
*G06K 9/62* (2006.01)
*G06T 7/00* (2006.01)
*G01N 15/10* (2006.01)

(52) U.S. Cl.
CPC .... *G06T 7/0081* (2013.01); *G01N 2015/1006* (2013.01); *G01N 2015/1486* (2013.01); *G06T 2207/30024* (2013.01); *G06T 2207/30242* (2013.01)

(56) References Cited

U.S. PATENT DOCUMENTS

| | | | | |
|---|---|---|---|---|
| 2004/0142411 | A1* | 7/2004 | Kirk | B01L 3/5025 435/33 |
| 2007/0038384 | A1* | 2/2007 | Kirk | G01N 33/5091 702/19 |
| 2008/0166035 | A1* | 7/2008 | Qian | G06T 7/0012 382/133 |
| 2008/0201083 | A1 | 8/2008 | Hata et al. | |
| 2008/0279441 | A1* | 11/2008 | Matsuo | G01N 15/1475 382/133 |
| 2010/0075406 | A1* | 3/2010 | Tanaka | C12M 23/14 435/287.1 |
| 2012/0149051 | A1* | 6/2012 | Kugelmeier | C12M 25/04 435/29 |

FOREIGN PATENT DOCUMENTS

| | | |
|---|---|---|
| JP | 2002218995 A | 8/2002 |
| JP | 2003021628 A | 1/2003 |
| JP | 2004344049 A | 12/2004 |
| JP | 2007124913 A | 5/2007 |
| JP | 2008076088 A | 4/2008 |
| JP | 2008261631 A | 10/2008 |
| WO | 2006101056 A1 | 9/2006 |
| WO | 2010103748 A1 | 9/2010 |
| WO | 2010143420 A1 | 12/2010 |
| WO | 2010146802 A1 | 12/2010 |
| WO | 2011013319 A1 | 2/2011 |

OTHER PUBLICATIONS

Hraha et al. "Dimensionality and Size Scaling of Coordinated Ca2D Dynamics in MIN6 b-cell Clusters", Biophysical Journal 106(1), Jan. 2014, pp. 299-309.*
N.H. Mahmood and M.A. Mansor. "Red Blood Cells Estimation Using Hough Transform Technique", SIPIJ 3(12), Apr. 2012, pp. 53-64.*
Y. Wang et al. "Segmentation of the Clustered Cells with Optimized Boundary Detection in Negative Phase Contrast Images", Plos One, Jun. 2015, pp. 1-19.*
Martin et al. "Computer based technique for cell aggregation analysis and cell aggregation in vitro chondrogenesis," Cytometry, Jul. 1997, p. 141-146.*
Sjollema et al. "Real-time enumeration of adhering microorganisms in a parallel plate flow cell using automated image analysis," Journal of Microbiological Methods, vol. 9, 1989, p. 73-78.*
Office Action issued Mar. 31, 2015, in corresponding Chinese Patent Application No. 201380007099.1 (6 pages).
International Search Report issued in PCT/JP2013/000290 mailed Apr. 16, 2013 (2 pages).
International Preliminary Report on Patentability and Written Opinion issued in PCT/JP2013/000290 mailed Aug. 14, 2014 (6 pages).
Extended European Search Report issued in corresponding European Application No. 13743827.1 dated Aug. 13, 2015 (5 pages).
Office Action issued in corresponding Chinese Application No. 201380007099.1 dated Jun. 7, 2016, and English translation thereof (6 pages).
Min, Wang. "Chapter 3 Animal Cell Engineering". Biological Engineering. 2nd Edition. Aug. 2009. (22 pages).

* cited by examiner

CELL COUNTING METHOD, CELL COUNTING DEVICE, AND COMPUTER-READABLE MEDIUM STORING CELL COUNTING PROGRAM

CROSS-REFERENCE TO RELATED APPLICATIONS

This application claims the benefit of International Patent Application No. PCT/JP2013/000290, filed on Jan. 22, 2013, which is incorporated by reference in its entirety.

TECHNICAL FIELD

The present invention relates to a method for counting cells. In particular, the present invention relates to a cell counting method, a cell counting device and a cell counting program that are capable of, when floating cells are cultured, counting cells during cultivation accurately without impairing proliferation efficiency.

BACKGROUND ART

In recent years, in the fields of production of medicines, gene therapy, regenerative medicine, immunotherapy or the like, it is required to cultivate efficiently a large amount of cells, tissues, microorganisms or the like in an artificial environment.

In such cultivation of a large amount of cells, when floating cells are cultured, there has been a demand for counting the number of cultured cells in order to grasp a change in the number of cells with the passage of time and a change in proliferation efficiency. However, conventionally, counting the number of cultured cells accurately encountered various problems.

Specifically, in proliferation of floating cells, there are cell clusters formed by three-dimensional aggregation of cells and individual cells that are present individually.

Conventionally, counting was conducted by a method wherein these cultured cells are photographed from above or from below, and then, based on the projected area of the cultured cells in an acquired image, the projected area of a cell cluster is divided by the average area of individual cells, whereby the number of cells is counted.

However, since a cell cluster is three-dimensional, the number of cells thus counted is smaller than the actual number of cells in a cell cluster. Further, if individual cells are assembled densely in a planar manner, the number of cells obtained by dividing the projected area of an individual cell by the average cell area of individual cells is counted in a number larger than the actual number of individual cells. Accordingly, there was a problem that the number of cells counted based on the projected area of the cultured cells is not accurate.

On the other hand, in order to obtain an accurate number of cells, it can be considered to count the number of cells by completely pulling apart a cell cluster.

However, in general, there is a further problem that excessive pulling apart of a cell cluster causes lowering of the proliferation efficiency. For this reason, conventionally, it was impossible to conduct accurate counting during cultivation, and an accurate counting was possible only at the time of collecting cells.

Here, as one of conventional methods of counting the number of cultured cells, the cell counting method disclosed in Patent Document 1 can be given. In this method, an observation image of cultured cells that are present in a culture container is acquired, and the ratio of an area occupied by cultured cells in the thus obtained observation image is calculated as an occupied area ratio. Then, based on the thus calculated occupied area ratio and a predetermined relational formula, the number of cultured cells present in the culture container is calculated.

RELATED ART DOCUMENT

Patent Document

Patent Document 1: JP-A-2007-124913

SUMMARY OF THE INVENTION

Problems to be Solved by the Invention

However, since this method is a method in which the number of cells is calculated based on the occupation area ratio, and hence, as mentioned above, it is impossible to conduct accurate counting. On the other hand, if a cell cluster is pulled apart in order to conduct accurate counting, the proliferation efficiency is lowered.

The present invention has been made in view of the above-mentioned circumstances, and is aimed at providing a cell counting method, a cell counting device and a cell counting program that are capable of counting the number of cells accurately without pulling apart cell clusters even if they are present, whereby an image of cultured cells during cultivation is acquired, an image of a cell cluster and an image of individual cells are separated from this image and the image of a cell cluster and the image of individual cells are subjected to an image processing separately, and the number of cells in a cell cluster and the number of individual cells are calculated respectively.

Means for Solving the Problems

In order to attain the above-mentioned object, the cell counting method of the present invention is a cell counting method for counting cultured cells, wherein an image of the cultured cells during cultivation is acquired;

an image of cell clusters and an image of individual cells are separated from this image; and based on each of the image of cell clusters and the image of individual cells, the number of cells in the cell cluster and the number of individual cells are calculated.

Further, the cell counting device of the present invention is a cell counting device for counting cultured cells, comprising:

means for acquiring an image of the cultured cells during cultivation;

means for separating an image of cell clusters and an image of individual cells from this image; and means for calculating the number of cells in the cell cluster and the number of the individual cells based on each of the image of cell clusters and the image of individual cells.

The cell counting program of the present invention is a cell counting program for counting cultured cells that allows a computer to execute:

inputting an image of the cultured cells during cultivation;

separating an image of cell clusters and an image of individual cells from this image; and calculating the number of cells in the cell cluster and the number of individual cells based on each of the image of cell clusters and the image of individual cells.

Advantageous Effects of the Invention

According to the present invention, it is possible to count accurately the number of cultured cells during cultivation without impairing the proliferation efficiency.

MODE FOR CARRYING OUT THE INVENTION

Hereinbelow, preferred embodiments of the cell counting method, the cell counting device and the cell counting program of the present invention will be explained with reference to the drawings.

Cell Counting Method

The cell counting method of the present invention will be explained with reference to FIGS. 1 to 6.

The cell counting method of this embodiment is a method for counting the number of cells cultured in a culture container. The method may be a method in which an image of a prescribed region of the culture container is acquired, and from this image, an image of a cell cluster and an image of individual cells are separated, and then, the image of a cell cluster and the image of individual cells are separately subjected to a image processing, whereby the number of cells in a cell cluster and the number of individual cells are respectively calculated. The method is not restricted by specific configurations of the embodiment and the examples. However, it can be a method having the following steps, for example.

(A) Acquisition of an Image of Cultured Cells

Figure 1:
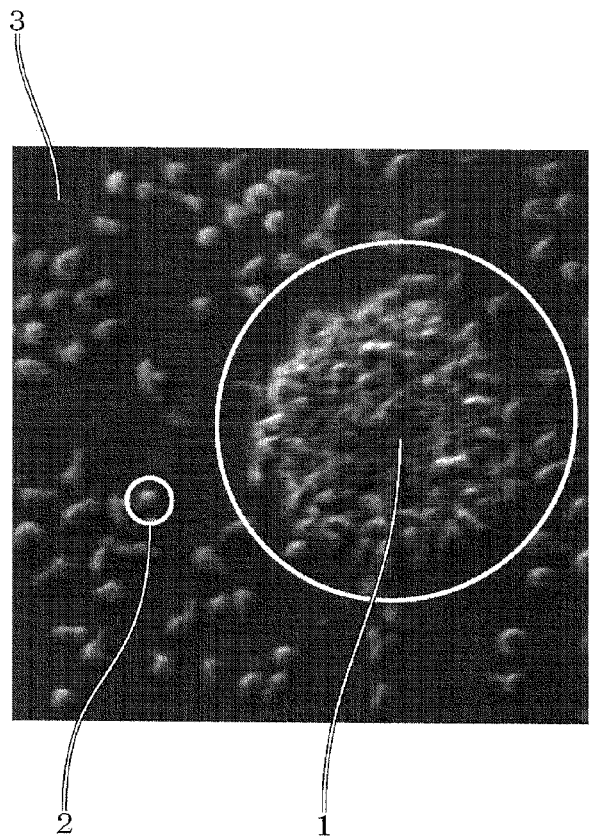
FIG. 1 is a view showing an image obtained by photographing floating cells that are cultured in a culture container from the direction of a bottom surface of a culture container.

First, by photographing a prescribed region of a culture container, an image is acquired. Specifically, for example, a transparent culture container is irradiated with light from above. Then, from below, by means of a camera through a microscope, cultured cells are photographed automatically, whereby an image of a prescribed region of the culture container can be acquired. Hereinafter, this image is often referred to as the "observation image". FIG. 1 is an observation image obtained by photographing the floating cells in the culture container. The figure shows how a cell cluster 1 and individual cells 2 are present in a culture liquid 3.

Alternatively, a method can be used in which only a prescribed region of the culture container is photographed, and after counting the number of cells in this region, based on the ratio of this region in the entire culture container, the number of cultured cells in the entire culture container can be calculated.

Figure 2:
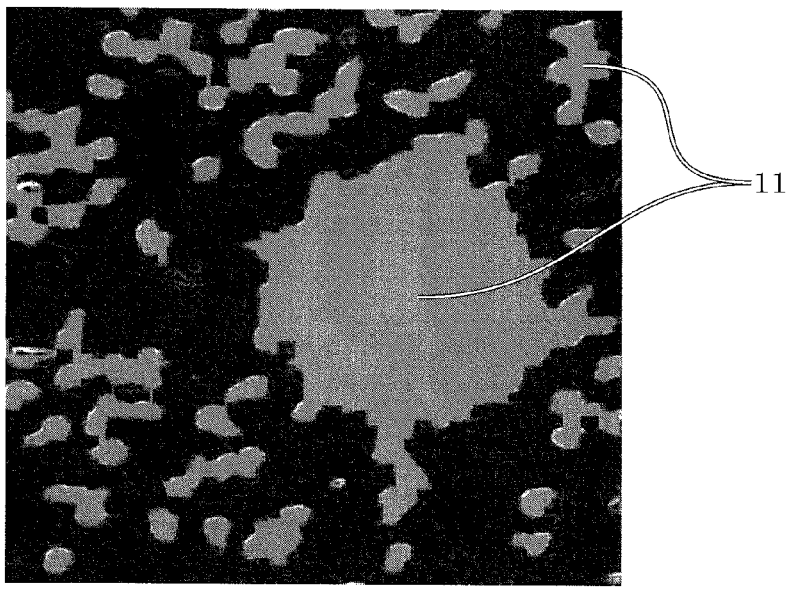
FIG. 2 is a view showing a projected area of cells in an image obtained by photographing floating cells that are cultured in a culture container from the direction of a bottom surface of a culture container.

Conventionally, by using this observation image, an image of the projected area of cells as shown in FIG. 2 is prepared, and the projected area 11 of the cells is divided by the average cell area of individual cells, whereby the number of cells is calculated. However, since the cell cluster 1 is three-dimensional, as for parts corresponding to the cell cluster 1, the number of cells counted in this parts is smaller than the actual number of cells. Further, as for parts corresponding to the individual cells 2, since parts in which the individual cells are connected with one another in a planar manner are also included in the projected area 11 of cells, the number of cells is counted in a number larger than the actual number. Therefore, in such a conventional method, it was not possible to count the number of cultured cells accurately.

(B) Separation of an Image of a Cell Cluster and an Image of Individual Cells

Next, an image of a cell cluster 1 and an image of individual cells 2 in the observation image are separated, whereby an image of the cell cluster and an image of the individual cells are separately prepared.

Figure 3:
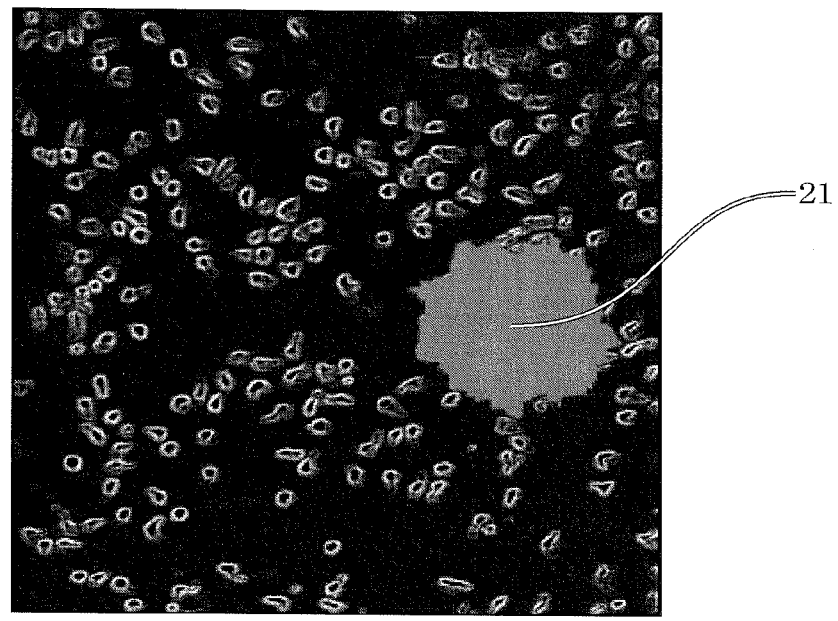
FIG. 3 is a view showing a projected area of a cell cluster obtained by separating individual cells and a cell cluster by using an image obtained by photographing floating cells being cultivated in a culture container.

Specifically, first, as shown in FIG. 3, an image of a cell cluster showing a projected area 21 of only the cell cluster 1 is prepared. Then, by using the image of the cell cluster, the cell projected area 21 of the cell cluster 1 is calculated.

Figure 4:
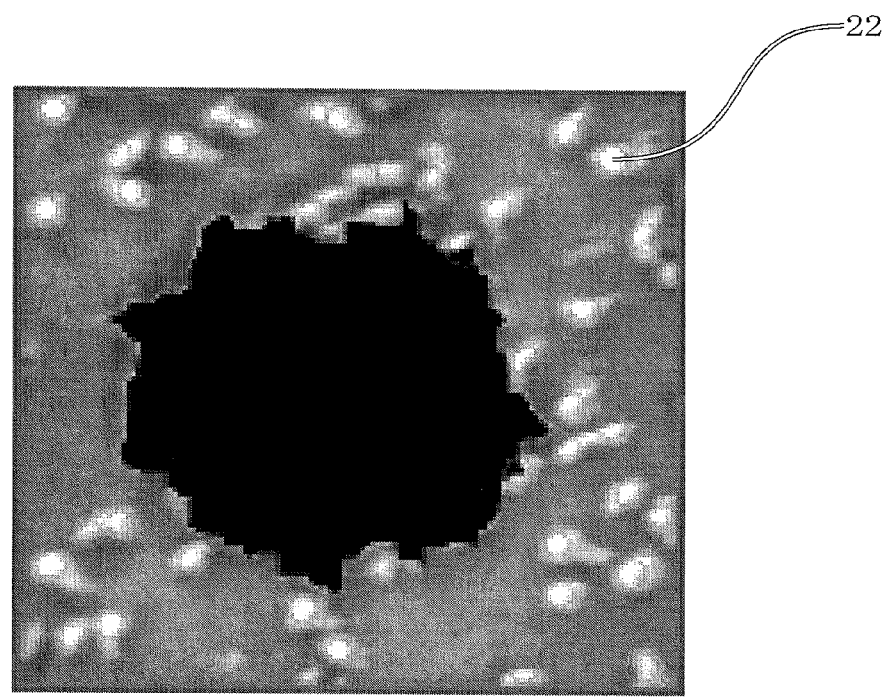
FIG. 4 is a view showing a projected area of an individual cell obtained by separating individual cells and cell clusters by using an image obtained by photographing floating cells being cultivated in a culture container.

Further, as shown in FIG. 4, the cell cluster 1 is deleted from the observation image, whereby an image of individual cells is prepared. Then, in order to allow the individual cells 2 to be counted individually, by using this image of individual cells, the individual cells 2 are subjected to a circular approximation processing in which individual cells 2 are approximated to circles such that they can be distinguished from each other. As a result, in the image of individual cells, the individual cells 22 that have been subjected to circular approximation are shown. By using this image of the individual cells, the number of the individual cells 2 is counted, and the average area of the individual cells 2 is calculated.

Figure 5:
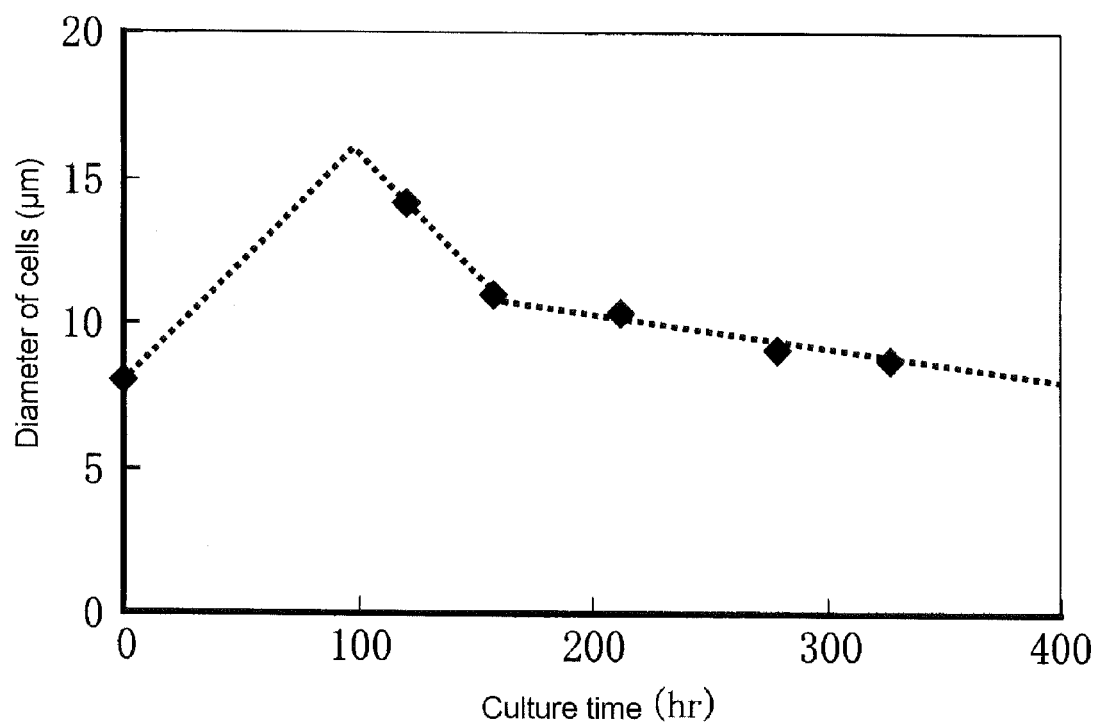
FIG. 5 is a view showing a change in diameter of individual cells in floating cells that are being cultivated.

Here, as shown in FIG. 5, the size of the cultured cells during cultivation may change according to the culture time. FIG. 5 shows a change in cell diameter when lymphocytic cells of a human being are proliferated.

As shown in FIG. 5, at the initial stage of cultivation, the diameter of the cultured cells is gradually increased. However, after the lapse of a predetermined period of time, a tendency is observed that the diameter is conversely decreased. Therefore, since the average area of individual cells changes according to the observation time, as mentioned above, it is preferred that the average area of individual cells be counted at the timing of counting the number of cultured cells.

On the other hand, as in the case of certain tumor cells, for example, there are some cultured cells of which the size does not change significantly during cultivation. In the case of these cultured cells, there is no need to count the average area of individual cells at the timing of counting the number of the cultured cells. That is, the average area of the individual cells is used for calculating the number of cells in the cell cluster (mentioned later). In the case of such cultured cells, it is preferable to set the volumes of individual cells in advance instead of calculating the average area, and to use these volumes for counting the number of cultured cells.

(C) Calculation of the Volume of a Cell Cluster

Subsequently, by using the cell projected area 21 obtained based on the image of the cell cluster, the volume of the cell cluster 1 is calculated as the volume of a sphere. Then, the volume of the square of the cell cluster 1 thus calculated is corrected by using the correction coefficient. Specifically, the volume of this sphere is divided by the correction coefficient, whereby the volume of the cell cluster 1 that is closer to the actual value can be obtained.

Figure 6:
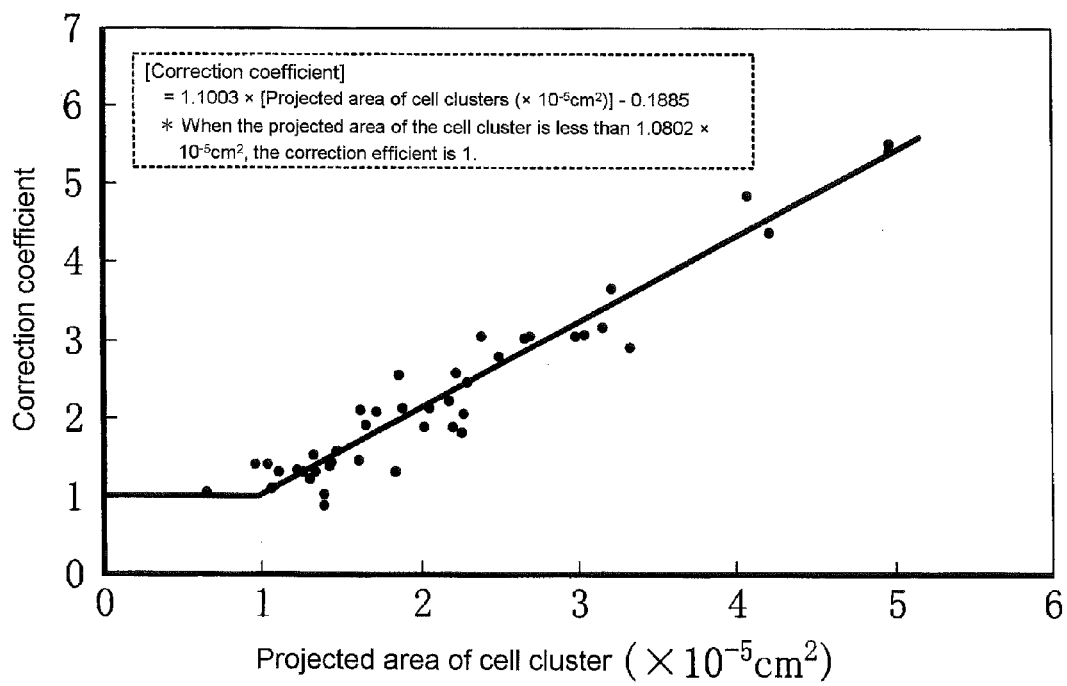
FIG. 6 is a view showing a correction coefficient of a volume of a cell cluster in floating cells that are being cultivated.

FIG. 6 shows a graph showing the relationship between the projected area of the cell cluster and the correction coefficient. This graph is obtained by plotting the projected area of the cell cluster against the volume of the cell cluster actually measured. Based on this graph, the relationship between the projected area of the cell cluster and the correction coefficient are expressed by a formula. That is, in this embodiment, the correction coefficient is determined by the following formula:

$$[\text{Correction coefficient}] = 1.1003 \times [\text{Projected area of cell clusters } (\times 10^{-5} \text{ cm}^2)] - 0.1885$$

When the projected area of the cell cluster is less than $1.0802 \times 10^{-5}$ cm$^2$, the correction efficient is 1.

The reason for correcting the volume of the cell cluster in this way is as follows. When the cell cluster is small, the cluster is present in an almost spherical shape. However, as the cell cluster grows bigger, the cell cluster is compressed longitudinally to have an elliptical longitudinal cross section. That is, with an increase in the cell projected area, the cell cluster has a further longitudinally compressed shape. This compression is corrected by using the correction coefficient. Since the correction coefficient may vary depending on the type of cells or the cultivation conditions, it is desirable to determine the correction coefficient in advance in accordance with these types or conditions.

(D) Calculation of the Number of Cells in the Cell Cluster

Subsequently, the volume of the cell cluster 1 obtained by correction is divided by the volume of the individual cell 2, whereby the number of cells in the cell cluster 1 is calculated. The volume of the individual cell 2 can be calculated based on the average area of the individual cells 2.

(E) Calculation of the Number of Cultured Cells

By the method mentioned above, the number of the individual cells 2 and the number of cells in the cell cluster 1 can be obtained. By adding these numbers, the number of cells in a region of the observation image can be calculated. Then, by multiplying the number of cells thus obtained by the ratio of the volume of the culture liquid in the region of the observation image to the volume of the total culture liquid, the number of cultured cells can be calculated.

Cell Counting Device and Cell Counting Program

Figure 7:
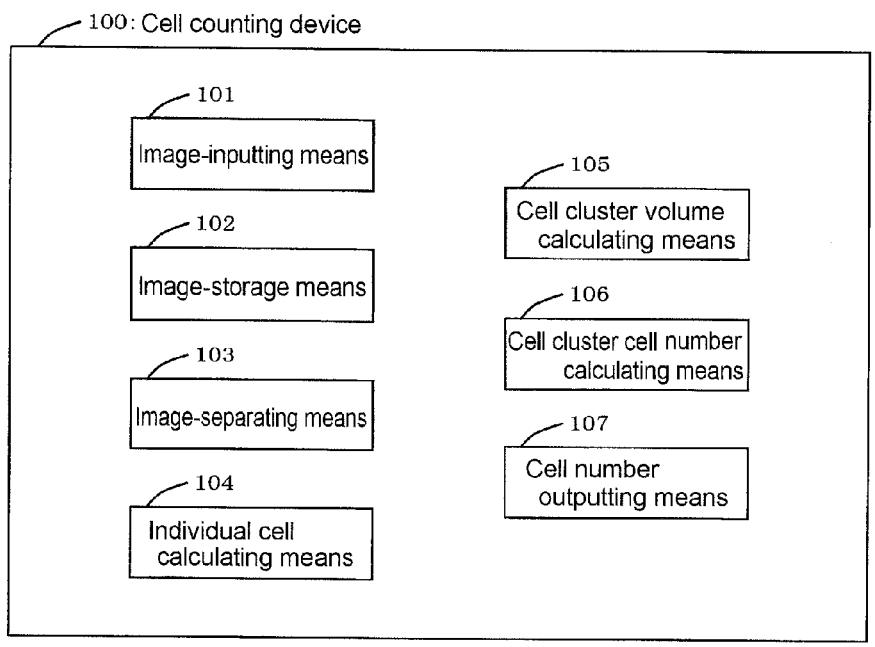
FIG. 7 is a block diagram showing the configuration of the cell counting device of the present invention.
Figure 8:
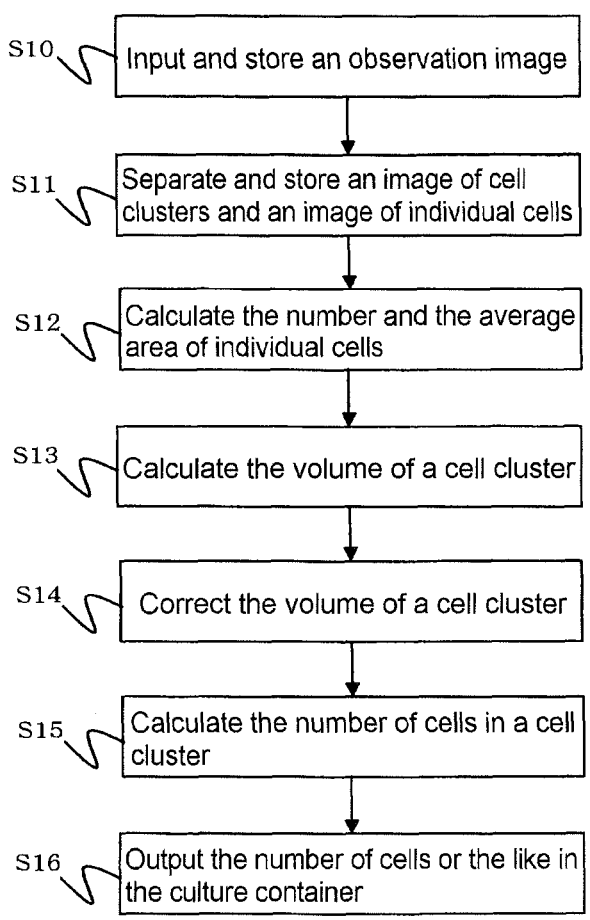
FIG. 8 is a flow chart showing a processing procedure of the cell counting program executed by the cell counting device of the present invention.

Subsequently, the cell counting device and the cell counting program of this embodiment will be explained with reference to FIGS. 7 and 8. FIG. 7 is a block diagram showing the configuration of the cell counting device of the present invention, and FIG. 8 is a flow chart showing a processing procedure by the cell counting program executed by the cell counting device of the present invention.

As shown in FIG. 7, a cell counting device 100 of this embodiment is provided with an image-inputting means 101, an image-storing means 102, an image-separating means 103, an individual cell calculating means 104, a cell cluster volume calculating means 105, a means 106 for calculating the number of cells in a cell cluster (hereinafter referred to as the cell cluster cell number calculating means 106) and a cell number outputting means 107. This cell counting device 100 can be configured by using various computers such as smartphones, tablet computers, personal computers, work stations and servers. Each of the above-mentioned configurations can be formed of a CPU, a memory or the like of a computer. Further, it can be configured as a dedicated counting device provided with each of these configurations.

The image-inputting means 101 inputs an image (observation image) obtained by automatically photographing cultured cells during cultivation by means of a camera and then stores the image in the image-storage means 102.

The image-separating means 103 separates the cell cluster and the individual cells in the observation image, prepare an image of the cell cluster and an image of individual cells, and then stores each image in the image-storage means 102.

The individual cell counting means 104 conducts circular approximation of individual cells by using the image of individual cells, and the number of the individual cells is counted. Further, the individual cell calculating means 104 also calculates the average area of the individual cells.

The cell cluster volume calculating means 105 calculates the projected area of a cell cluster by using the image of a cell cluster. Further, the cell cluster volume calculating means 105 calculates by multiplying the volume of the cell cluster that is assumed to be a sphere by a correction coefficient.

The cell cluster cell number calculating means 106 divides the volume of the cell cluster calculated by the cell cluster volume calculating means 105 by the volume of an individual cell, whereby the number of cells in the cell cluster is calculated. At this time, the cell cluster cell number calculating means 106 calculates the volume of an individual cell based on the average area of individual cells calculated by means of the individual cell calculating means 104.

The cell number outputting means 107 calculates, as the number of cells in a region in the observation area, the sum of the number of individual cells calculated by the individual cell calculating means 104 and the number of cells in the cell cluster calculated by the cell cluster cell number calculating means 106. Further, the cell number outputting means 107 can multiply the number of cells in the region of this observation image by the ratio of the volume of the culture liquid in the observation image to the volume of the total culture liquid, thereby to calculate the number of cells in the culture liquid.

Then, the cell number outputting means 107 outputs the number of cells in the region in the observation image and/or the number of cells in the culture liquid to a display device (not shown) connected to the cell counting device 100.

Subsequently, the procedure in the cell counting device 100 will be explained with reference to FIG. 8. FIG. 8 is a flow chart showing the procedure by the cell counting program executed by the cell counting device 100 according to one embodiment of the present invention. That is, the cell counting program of this embodiment allows the cell counting device 100 such as a computer to execute the following procedure.

First, the image-inputting means 101 in the cell counting device 100 inputs an observation image photographed by a camera, and stores the image in the image-storing means 101 (step 10).

Subsequently, the image-separating means 103 in the cell counting device 100 separates an image of a cell cluster 1 and an image of individual cells 2 by using an observation image, thereby preparing both an image of a cell cluster and an image of individual cells, and stores them in the image-storing means 102 (step 11).

Then, by using the image of individual cells, the individual cell calculating means 104 in the cell counting device 100 conducts circular approximation of individual cells, and the number of individual cells is counted. Further, the average area of individual cells is calculated (step 12).

Further, the cell cluster volume calculating means 105 in the cell counting device 100 calculates the projected area of a cell cluster by using an image of a cell cluster. Then, by using this projected area, the volume of a cell cluster is calculated on the assumption that the cluster is spherical (step 13).

Further, this cell cluster volume calculating means 105 corrects the thus calculated volume of the sphere, whereby the volume of a cell cluster that is closer to the actual volume is calculated (step 14).

Then, the cell cluster cell number calculating means 106 in the cell counting device 100 divides the volume of the cluster of cells by the volume of an individual cell, whereby the number of cells in a cell cluster in a region of the observation image is calculated (step 15).

By the above-mentioned procedure, the number of cells in a cell cluster and the number of individual cells can be calculated more accurately, and hence, the number of cultured cells can be grasped more accurately.

Finally, the cell number outputting means 107 in the cell counting device 100 calculates the total of the number of cells in a cell cluster and the number of individual cells, whereby the number of cells in a region of the observation image is calculated. Further, the thus obtained number of cells is converted to the number of cells in the entire culture container. Then, the cell number outputting means 107 outputs the number of cells in the culture container to a display device (step 16).

As explained hereinabove, conventionally, there was a problem that, when a cell cluster having a size larger than a certain size is formed, the number of cells cannot be counted accurately, and hence, counting can be substantially conducted only after the cultivation.

However, according to this embodiment, the number of cells in a cluster of cells can be counted accurately. Further, as for individual cells, more accurate counting as compared with conventional methods can become possible. Accordingly, the number of cells during cultivation can be grasped further accurately.

As a result, the history of cell proliferation can be recorded, and hence, the state of cells during cultivation can be grasped.

Further, since the number of cells during cultivation can be grasped by the cell counting device of this embodiment, variations caused by visual observation can be eliminated, whereby timing of subculture can be judged more accurately.

EXAMPLES

Example 1

By using the cell counting method, the cell counting device and the cell counting program of the above-mentioned embodiment, the number of the cells during cultivation in a culture container was counted.

Specifically, as the culture container, an LLDPE-made bag (thickness: 100 µm, dimension 230×620 mm) was used. As the culture medium, AlyS505N-7 (Cell Science & Technology) was used. As the seeding cells, $6.4 \times 10^6$ cells of human mononuclear cells from peripheral blood was seeded. After the lapse of 66 hours, 104 hours, 174 hours, 222 hours and 234 hours from the start of cultivation, the number of cultured cells was counted.

Figure 9:
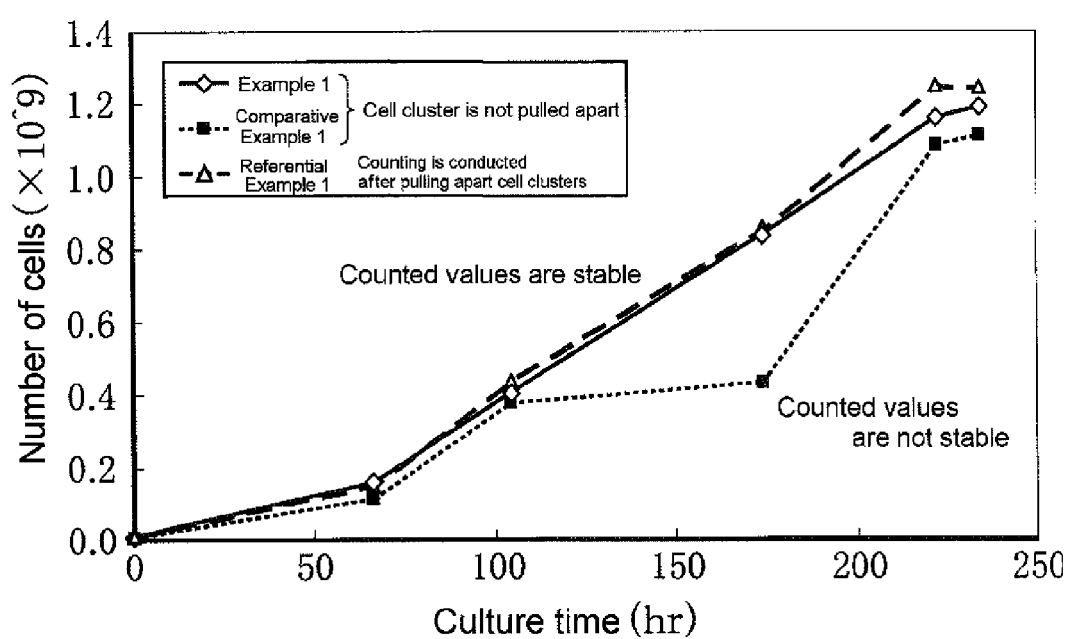
FIG. 9 is a view showing a graph showing the results of counting of floating cells being cultivated in a culture container, comparing the cell counting method of the present invention and the conventional cell counting method.

As a result, as shown in FIG. 9, it was found that the number of cells counted in Example 1 was $1.60 \times 10^8$ cells, $4.07 \times 10^8$ cells, $8.41 \times 10^8$ cells, $1.16 \times 10^9$ cells and $1.19 \times 10^9$ cells, respectively.

Comparative Example 1

By using the same culture container and the same culture cells as those used in Example 1, the number of the culture cells was counted by a conventional method at the same timing as that in Example 1. Specifically, by using an observation photograph of cultured cells obtained by photographing a predetermined region of the culture container, an image of the projected area of cells was obtained. Then, the projected area of the cell was calculated, and the resulting projected area was divided by the average area of individual cells, thereby to calculate the number of cells.

As a result, as shown in FIG. 9, the number of cells counted in Comparative Example 1 was $1.12 \times 10^8$ cells, $3.79 \times 10^8$ cells, $4.34 \times 10^8$ cells, $1.08 \times 10^9$ cells, $1.11 \times 10^9$ cells, respectively.

Referential Example 1

When cells were cultured and the number of the cells was counted under the same conditions as those in Example 1, counting was conducted after putting apart all cell clusters to be individual cells. At this time, by using an observation image obtained by photographing a prescribed region of the culture container, individual cells were subjected to circular approximation, whereby the number of cells was counted.

A different culture container was prepared for each time of counting, i.e. a single container was used for a single counting. Accordingly, in this Referential Example, it can be considered that no adverse effects were exerted on the proliferation efficiency by pulling apart of cell clusters and, at each counting timing, accurate counting results relatively closer to the actual number of cells can be obtained.

The number of cells counted in Referential Example 1 was, as shown in FIG. 9, $1.45 \times 10^8$ cells, $4.34 \times 10^8$ cells, $8.48 \times 10^8$ cells, $1.25 \times 10^9$ cells and $1.24 \times 10^9$ cells, respectively.

As mentioned hereinabove, according to the conventional cell counting method in Comparative Example 1, the counted values are not stable, revealing that an accurate counting was not conducted. For example, as for the value after the lapse of 174 hours, the counted value is significantly smaller than the counted values in Example 1 and Referential Example 1. The reason therefor is assumed that the cluster of cultured cells has increased in size. On the contrary, according to the cell counting method, the cell counting device and the cell counting program of this embodiment (demonstrated in Example 1), even if the number of cells is counted without pulling apart cell clusters, accurate counting that is almost equivalent to counting that is conducted after putting apart all cell clusters to be totally individual cells can be conducted.

The present invention is not restricted by the embodiment mentioned above or the Examples, and it is needless to say that various modifications are possible within the scope of the present invention.

For example, in the above-mentioned embodiment, the project are of only cell clusters is calculated and then the number of individual cells and the average area of cells are measured. This order may be reverse. Further, appropriate modifications are possible, for example, the correction coefficient may be varied according to the number of cells or cultivation conditions.

INDUSTRIAL APPLICABILITY

The present invention can be preferably applied in a field where a large amount of cells are required to be cultured, such as biological medical therapy, regenerative medical therapy and the immunotherapy.

The invention claimed is:

1. A cell counting method for counting cultured cells, comprising:
    acquiring an image of the cultured cells;
    separating an image of cell clusters and an image of individual cells from the image of the cultured cells;
    conducting circular approximation of the individual cells based on the image of the individual cells;
    calculating a number of the individual cells and an average area of the individual cells;
    calculating a volume of the cell cluster based on a projected area of the cell cluster that is assumed to be a sphere;
    calculating a volume of the individual cells based on the average area of the individual cells; and
    dividing the volume of the cell cluster by the volume of the individual cell, wherein
    the volume of the cell cluster is further divided by a correction coefficient selected from:
    (a) correction coefficient=$1.1003\times$[the projected area of the cell cluster ($\times 10^{-5}$ cm$^2$)]$-0.1885$ when the projected area of the cell cluster is greater than or equal to $1.0802\times 10^{-5}$ cm$^2$, or
    (b) correction coefficient=1 when the projected area of the cell cluster is less than $1.0802\times 10^{-5}$ cm$^2$.

2. The cell counting method according to claim 1, wherein
    the volume of the individual cell is set in advance;
    the volume of the cell cluster is calculated based on the projected area of the cell cluster; and
    the volume of the cell cluster is divided by the volume of the individual cell that is set in advance, whereby a number of cells in the cell cluster is calculated.

3. The cell counting method according to claim 1, wherein the cultured cells are floating cells.

4. The cell counting method according to claim 3, wherein the floating cells are leukocytes.

5. A cell counting device for counting cultured cells, comprising:
    a camera that acquires an image of the cultured cells;
    one or more central processing units (CPU) that:
        separate an image of cell clusters and an image of individual cells from the image of the cultured cells;
        conduct circular approximation of the individual cells based on the image of the individual cells;
        calculate a number of the individual cells and an average area of the individual cells;
        calculate a volume of the cell cluster based on a projected area of the cell cluster that is assumed to be a sphere;
        calculate a volume of the individual cells based on the average area of the individual cells; and
    divide the volume of the cell cluster by the volume of the individual cell, wherein
    the volume of the cell cluster is further divided by a correction coefficient selected from:
    (a) correction coefficient=$1.1003\times$[the projected area of the cell cluster ($\times 10^{-5}$ cm$^2$)]$-0.1885$ when the projected area of the cell cluster is greater than or equal to $1.0802\times 10^{-5}$ cm$^2$, or
    (b) correction coefficient=1 when the projected area of the cell cluster is less than $1.0802\times 10^{-5}$ cm$^2$.

6. The cell counting device according to claim 5, wherein the cultured cells are floating cells.

7. The cell counting device according to claim 6, wherein the floating cells are leukocytes.

8. A non-transitory computer-readable medium storing instructions for counting cultured cells that cause a computer to execute:
    inputting an image of the cultured cells;
    separating an image of cell clusters and an image of individual cells from the image of the cultured cells; and
    conducting circular approximation of the individual cells based on the image of the individual cells;
    calculating a number of the individual cells and an average area of the individual cells;
    calculating a volume of the cell cluster based on a projected area of the cell cluster that is assumed to be a sphere;
    calculating a volume of the individual cells based on the average area of the individual cells; and
    dividing the volume of the cell cluster by the volume of the individual cell, wherein
    the volume of the cell cluster is further divided by a correction coefficient selected from:
    (a) correction coefficient=$1.1003\times$[the projected area of the cell cluster ($\times 10^{-5}$ cm$^2$)]$-0.1885$ when the projected area of the cell cluster is greater than or equal to $1.0802\times 10^{-5}$ cm$^2$, or
    (b) correction coefficient=1 when the projected area of the cell cluster is less than $1.0802\times 10^{-5}$ cm$^2$.

9. The non-transitory computer-readable medium according to claim 8, wherein the cultured cells are floating cells.

10. The non-transitory computer-readable medium according to claim 9, wherein the floating cells are leukocytes.

* * * * *